US010363280B2

(12) United States Patent
Vaughan et al.

(10) Patent No.: US 10,363,280 B2
(45) Date of Patent: *Jul. 30, 2019

(54) NUTRACEUTICAL GELS

(71) Applicant: 4Life Patents, LLC, Sandy, UT (US)

(72) Inventors: Brent M. Vaughan, Draper, UT (US); Calvin W. MacCausland, Springville, UT (US); David A. Lisonbee, Orem, UT (US)

(73) Assignee: 4Life Patents, LLC, Sandy, UT (US)

( * ) Notice: Subject to any disclaimer, the term of this patent is extended or adjusted under 35 U.S.C. 154(b) by 854 days.

This patent is subject to a terminal disclaimer.

(21) Appl. No.: 14/710,472

(22) Filed: May 12, 2015

(65) Prior Publication Data

US 2016/0000853 A1    Jan. 7, 2016

Related U.S. Application Data

(63) Continuation of application No. 12/436,062, filed on May 5, 2009, now Pat. No. 9,028,882, which is a continuation-in-part of application No. 11/415,837, filed on May 2, 2006, now Pat. No. 9,956,258, and a continuation-in-part of application No. 11/855,944, filed on Sep. 14, 2007.

(60) Provisional application No. 60/677,226, filed on May 2, 2005, provisional application No. 60/848,348, filed on Sep. 29, 2006.

(51) Int. Cl.

| A61K 36/889 | (2006.01) |
|---|---|
| A23G 4/12 | (2006.01) |
| A61K 36/185 | (2006.01) |
| A61K 36/35 | (2006.01) |
| A61K 36/87 | (2006.01) |
| A61K 47/36 | (2006.01) |
| A23L 29/231 | (2016.01) |
| A23L 29/238 | (2016.01) |
| A23L 29/269 | (2016.01) |
| A23L 29/281 | (2016.01) |
| A23L 33/10 | (2016.01) |
| A23L 33/105 | (2016.01) |

(52) U.S. Cl.
CPC .............. *A61K 36/889* (2013.01); *A23G 4/12* (2013.01); *A23L 29/231* (2016.08); *A23L 29/238* (2016.08); *A23L 29/27* (2016.08); *A23L 29/271* (2016.08); *A23L 29/284* (2016.08); *A23L 33/10* (2016.08); *A23L 33/105* (2016.08); *A61K 36/185* (2013.01); *A61K 36/35* (2013.01); *A61K 36/87* (2013.01); *A61K 47/36* (2013.01); *A23V 2002/00* (2013.01); *A23V 2200/324* (2013.01); *A23V 2250/21* (2013.01); *A23V 2250/21166* (2013.01); *A23V 2250/506* (2013.01); *A23V 2250/5086* (2013.01); *A23V 2250/708* (2013.01); *A61K 2300/00* (2013.01)

(58) Field of Classification Search
None
See application file for complete search history.

(56) References Cited

U.S. PATENT DOCUMENTS

| 3,692,532 | A | | 9/1972 | Shenkenberg et al. |
|---|---|---|---|---|
| 3,851,051 | A | * | 11/1974 | Miskel ................ A61K 9/0056 206/524.8 |
| 4,810,827 | A | * | 3/1989 | Mitsuhashi ........... A23L 3/3463 127/30 |
| 4,816,563 | A | | 3/1989 | Wilson et al. |
| 5,252,333 | A | | 10/1993 | Horrobin |
| 5,585,098 | A | | 12/1996 | Coleman |
| 5,648,092 | A | * | 7/1997 | Weckenmann ...... A61K 9/0056 424/464 |
| 5,773,232 | A | | 6/1998 | Wier |
| 5,846,532 | A | | 12/1998 | Kline |
| 5,928,686 | A | | 7/1999 | Ivey et al. |
| 6,030,622 | A | | 2/2000 | Shehadeh |
| 6,147,624 | A | | 11/2000 | Clapper |
| 6,210,681 | B1 | | 4/2001 | Walker et al. |
| 6,258,383 | B1 | | 7/2001 | Gohlke et al. |
| 6,326,028 | B1 | | 12/2001 | Nivaggioli et al. |
| 6,468,534 | B1 | | 10/2002 | Hennen et al. |
| 6,630,316 | B1 | | 10/2003 | Wier |
| 6,733,781 | B2 | | 5/2004 | Abu-Izza et al. |
| 6,811,793 | B2 | | 11/2004 | Wehling |
| 6,866,868 | B1 | | 3/2005 | Lisonbee et al. |
| 7,094,415 | B2 | | 8/2006 | Marenick |

(Continued)

FOREIGN PATENT DOCUMENTS

| CN | 1583164 A | 2/2005 |
|---|---|---|
| DE | 121707 A | 8/1976 |

(Continued)

OTHER PUBLICATIONS

International Search Report, PCT/US2006/017118, dated Sep. 13, 2006.
"Announcing 4Life Transfer Factor RioVida with Acai Berry," http://web.archive.org/web/20050413042215/http://www.acaiberries.com/index.html, accessed Oct. 25, 2007.
"Food Protection Program," http://archive.org/web/20040221222150/ http://www.metrokc.gov/health/foodsfty/pasturizedjuice.htm, Feb. 21, 2004, accessed Oct. 25, 2007.
Slater, "Who's Drinking What," Sunday Times, London, May 16, 2004, p. 44.

(Continued)

*Primary Examiner* — Amy L Clark
(74) *Attorney, Agent, or Firm* — Durham Jones & Pinegar, P.C., Intellectual Property Law Group

(57) ABSTRACT

A nutraceutical food product includes a solid matrix and a liquid combined into a gel. The nutraceutical food product may include an immune modulator, such as transfer factor and/or a nanofraction immune modulator. A fruit component may be included in the nutraceutical food product. The fruit component may include at least one oligoproanthocyanidin-containing fruit, such as açai.

17 Claims, No Drawings

(56) References Cited

U.S. PATENT DOCUMENTS

| | | | |
|---|---|---|---|
| 7,169,571 | B2 | 1/2007 | Wier |
| 2002/0034563 | A1 | 3/2002 | Grassin et al. |
| 2002/0044942 | A1 | 4/2002 | Dopson |
| 2003/0077254 | A1* | 4/2003 | Ramaekers ............ A61K 31/19 424/93.3 |
| 2007/0098869 | A1 | 5/2007 | Foster et al. |
| 2008/0081076 | A1 | 4/2008 | Lisonbee et al. |
| 2009/0162517 | A1 | 6/2009 | Lai et al. |

FOREIGN PATENT DOCUMENTS

| | | | | |
|---|---|---|---|---|
| EP | 1 106 068 A2 | 6/2001 | | |
| EP | 1 602 653 A1 | 12/2005 | | |
| JP | 2005-068060 | 3/2005 | | |
| JP | 2005527234 | 9/2005 | | |
| JP | 2006-520804 | 9/2006 | | |
| JP | 2007-505913 | 3/2007 | | |
| WO | 1997020548 A1 | 6/1997 | | |
| WO | 2000059519 A2 | 10/2000 | | |
| WO | WO-0217732 A2 * | 3/2002 | ........... | A61K 31/352 |
| WO | 2003101225 A2 | 12/2003 | | |
| WO | 2004017916 A2 | 3/2004 | | |
| WO | 2004041071 A2 | 5/2004 | | |
| WO | 2004080995 A1 | 9/2004 | | |
| WO | 2004084833 A2 | 10/2004 | | |
| WO | WO-2004084833 A2 * | 10/2004 | ........... | A61K 36/889 |
| WO | 2004112491 A2 | 12/2004 | | |
| WO | 2005028622 A2 | 3/2005 | | |
| WO | 2006119408 A1 | 11/2006 | | |

OTHER PUBLICATIONS

International Search Report, PCT/US2007/078947, dated Aug. 22, 2008.
Bates, R.P., et al., "Principles and Practices of Small and Medium Scale Fruit Juice Processing," Food and Agricultural Organization of the United Nations (FAO) Services Bulletin 146 (Rome, 2001).
Hoover, D.G., "Minimally Processed Fruits and Vegetables: Reducing Microbial Load by Nonthermal Physical Treatments," Food Tech. 57(6): 66-69, 71 (1997).
Peters, R.L., et al., "Assay in the Mouse for Delayed-Type Hypersensitivity to Murine Leukemia Virus," J. Natl. Cancer Inst. 55(5): 1089-95 (Nov. 1975).
Beecher, G.R., "Proanthocyanidins: Biological Activities Associated with Human Health," Pharmaceutical Biol. 42 (Supplement): 2-20 (2004).
"RioVida—Liquid Transfer Factor in Acai Berry Juice," http://web.archive.org/web/20050416024521/http://www.globalsuccess4life.com/riovida.html, Apr. 16, 2005, accessed Jun. 8, 2013.
European Patent Office, Supplementary European Search Report of Jul. 24, 2009 in corresponding European application No. 06759033.1, which is a national stage application corresponding to International Application PCT/US2006/017118.
Brown, T.A., "Immunity at Mucosal Surfaces," Advances in Dental Research 10:62 (1996).
Strunz, U. "Forever Young: Fitness Drinks: Get Fit, Stay Young and Keep Slender with Protein-packed Power Drinks," Silverback Books, pp. 23 and 34 (2001).
Wolfe, F.A., "The Complete Idiot's Guide to Herbal Remedies," p. 146 (Penquin, 1999).
Mazo, "The Immune Advantage: The Powerful, Natural Immune-boosting Program to Help you Prevent Disease, Enhance Vitality, Live Longer, Healthier Life," p. 307 (Rodale,2001).
Birklin, M. "Prevention Magazine's Nutrition Advisor: The Ultimate Guide to Health-Boosting and Health-Harming Factors in Your Diet," p. 301 (Rodale, 1994).
Challem, J. "User's Guide to Nutritional Supplements," p. 261 (Basic Health Publications, Inc., 2003).
dictionary.reference.com, http://dictionary.reference.com/browse/food, Accessed Oct. 25, 2011.
Danish Patent and Trademark Office, "Singapore Search Report and Written Opinion," dated May 17, 2013, in related Singapore application No. 201100707-7.
Hagerman, A.E., et al., "the Specificity of Proanthocyanidin Protein Interactions," J. Biol. Chem., 256(9): 4494-97 (1981).
IP Australia, Examiner's Report dated Mar. 25, 2011 in related Australian application No. 2006242106.
State Intellectual Property Office of China, English translation of First Office Action dated Aug. 10, 2010 in related Chinese application No. 200680021004.1.
State Intellectual Property Office of China, English translation of Second Office Action dated Jan. 11, 2012 in related Chinese application No. 200680021004.1.
State Intellectual Property Office of China, English translation of Notification of Reexamination dated Aug. 3, 2013 in related Chinese application No. 200680021004.1.
State Intellectual Property Office of China, English translation of First Office Action dated Aug. 1, 2016 in related Chinese application No. 201410247204.5.
State Intellectual Property Office of China, English translation of Second Office Action dated Jun. 16, 2017 in related Chinese application No. 201410247204.5.
State Intellectual Property Office of China, English translation of Third Office Action dated Jan. 5, 2018 in related Chinese application No. 201410247204.5.
European Patent Office, Communication pursuant to Article 94(3) EPC dated Jun. 11, 2009 in related European application No. 06759033.1.
European Patent Office, Communication pursuant to Article 94(3) EPC dated Jan. 27, 2011 in related European application No. 06759033.1.
European Patent Office, Communication pursuant to Article 94(3) EPC dated Mar. 28, 2012 in related European application No. 06759033.1.
European Patent Office, Communication pursuant to Article 94(3) EPC dated Mar. 10, 2014 in related European application No. 06759033.1.
European Patent Office, Communication pursuant to Article 94(3) EPC dated Feb. 3, 2015 in related European application No. 06759033.1.
European Patent Office, Communication pursuant to Article 94(3) EPC dated Oct. 19, 2016 in related European application No. 06759033.1.
Japanese Patent Office, English Translation of Sep. 3, 2010 of First Office Action in related Japanese application No. 2008-510197.
Japanese Patent Office, English Translation of Apr. 8, 2011 of Second Office Action in related Japanese application No. 2008-510197.
Japanese Patent Office, English Translation of Dec. 27, 2011 of Third Office Action in related Japanese application No. 2008-510197.
Mexican Patent Office, English Summary dated Jan. 10, 2011 of First Office Action in related Mexican application No. MX/a/2007/013850.
Mexican Patent Office, English Summary dated Jun. 21, 2010 of Second Office Action in related Mexican application No. MX/a/2007/013850.
Intellectual Property Office of the Philippines, Bureau of Patents, Substantive Examination Report dated Apr. 2, 2012 in related Filipino application No. 1/2007/502430.
Intellectual Property Office of the Philippines, Bureau of Patents, Subsequent Substantive Examination Report dated May 17, 2013 in related Filipino application No. 1/2007/502430.
Intellectual Property Office of the Philippines, Bureau of Patents, Subsequent Substantive Examination Report dated Aug. 23, 2013 in related Filipino application No. 1/2007/502430.
Xiang, C, et al, "P-transfer factor for oral solution," Pediatric Drug Handbook 241 (Beijing Science Press 2002-2007).
Chuanhe, T., Bioactive Substance from Plants 275 & 288 (Chemical Industry Press, Jan. 31, 2005).

* cited by examiner

NUTRACEUTICAL GELS

CROSS-REFERENCE TO RELATED APPLICATIONS

This application is a continuation of U.S. patent application Ser. No. 12/436,062, filed on May 5, 2009, and titled NUTRACEUTICAL GELS, issued as U.S. Pat. No. 9,028,882 on May 12, 2015, which is a continuation-in-part of U.S. patent application Ser. No. 11/415,837, filed May 2, 2006, pending, which claims the benefit of priority under 35 U.S.C. § 119(e) to the filing date of U.S. Provisional Patent Application Ser. No. 60/677,226, filed May 2, 2005, for TRANSFER FACTOR PREPARATIONS AND ASSOCIATED METHODS. This application is also a continuation-in-part of U.S. patent application Ser. No. 11/855,944, filed Sep. 14, 2007, pending, which claims the benefit of priority under 35 U.S.C. § 119(e) to the filing date of U.S. Provisional Patent Application Ser. No. 60/848,348, filed Sep. 29, 2006, for IMMUNE MODULATORS, PREPARATIONS AND COMPOSITIONS INCLUDING IMMUNE MODULATORS, TESTS FOR EVALUATING THE ACTIVITY OF IMMUNE MODULATORS AND PREPARATIONS AND COMPOSITIONS INCLUDING THE SAME, AND METHODS. The entire disclosure of each of the foregoing applications is hereby incorporated by reference.

TECHNICAL FIELD

The present invention relates generally to natural supplements, or nutraceutical food products and, more specifically, to gel-based nutraceutical food products. The nutraceutical food products to which the present invention relates may include an immune modulator, such as transfer factor or a nanofraction immune modulator, which may be distributed throughout a gel-based matrix. The present invention also relates to acai-based nutraceutical products.

SUMMARY

The present invention includes various embodiments of a nutraceutical food product in the form of a gel, or a semirigid colloidal dispersion of a solid matrix with a liquid. Some embodiments of a nutraceutical food product of the present invention include an immune modulator, which may be distributed throughout the solid matrix. The immune modulator may comprise transfer factor and/or a nanofraction immune modulator of the type described in U.S. patent application Ser. No. 11/855,944, filed Sep. 14, 2007, the entire disclosure of which is, by this reference, incorporated herein. When distributed throughout the gel, the immune modulator may retain substantially all of one or more of its activities (e.g., components of the liquid component may not interfere with one or more activities of the immune modulator), or one or more of the activities of the immune modulator may actually be enhanced by one or more components of the gel component of the nutraceutical food product.

Various embodiments of nutraceutical food products of the present invention include a fruit component. The fruit component may include at least one oligoproanthocyanidin ("OPC")-containing fruit or an extract thereof. The term "extract" is broadly defined herein, including any OPC-including part of a fruit. Examples of extracts include, without limitation, juices (dilute, normal concentration, or concentrate), dehydrated fruit, and powders including one or more components of the fruit. In some embodiments of such a nutraceutical food product, at least some of the fruit component is present in liquid form. In some embodiments, at least some of the fruit component may be included in the nutraceutical food product in solid form, where it may be incorporated into the gel matrix or merely reside within voids of the gel matrix, where it may be distributed throughout the gel matrix (e.g., as a fruit pectin).

Another aspect of the present invention includes a process for making an edible preparation that includes an immune modulator, such as transfer factor and/or a nanofraction immune modulator. The process includes mixing a fruit component with the immune modulator. Preservatives may also be included in the mixture. The mixture may be chilled to prevent microbial growth. To further prevent microbial growth, the mixture may be pasteurized before chilling. Alternatively, the mixture may be sterilized.

Other features and advantages of the present invention will become apparent to those of ordinary skill in the art through consideration of the ensuing description and the appended claims.

DETAILED DESCRIPTION

In an exemplary embodiment of a gel-based nutraceutical food product, the gel comprises a solid polymeric matrix throughout which a liquid is dispersed.

The solid polymeric matrix may comprise a galactomannan, a polysaccharide (e.g., xanthan, a fruit pectin, etc.), gelatin, or any other suitable gelling agent. In some embodiments, a plurality of gelling agents are used to provide desired properties, such as viscosity, consistency, and edibility.

Various embodiments of nutraceutical food products that incorporate teachings of the present invention include a fruit component. The fruit component includes at least one fruit that naturally includes OPC or a juice or other extract of such a fruit. By way of nonlimiting example, the fruit component may include one or more of açai, elderberry, grape, and pomegranate, or an extract thereof. OPC is a known antioxidant and may, therefore, be useful in neutralizing or otherwise acting against free radicals and other oxidants, which may adversely affect cell membranes, cause accelerated cellular aging, and are known or believed to be at least indirectly responsible for a wide variety of disease states, as well as compromised immunity, in living beings.

In embodiments of nutraceutical food products that include fruit components, the fruit component may be in solid form, in liquid form, or in some combination of solid and liquid forms. When the fruit component is included in solid form, it may be incorporated into the matrix (e.g., as pectin, such as pectin of an OPC-containing fruit, etc.) or it may be dispersed throughout the matrix (e.g., as chunks, bits, etc.).

An immune modulator may be present within (e.g., dispersed throughout, dissolved in, etc.) the liquid component of various embodiments of nutraceutical food products of the present invention. When mixed with the liquid component, the immune modulator may retain substantially all of one or more of its activities (e.g., components of the liquid component may not interfere with one or more activities of the immune modulator), or one or more of the activities of the immune modulator may actually be enhanced by one or more components of the liquid component of the nutraceutical food product.

The immune modulator may include transfer factor. The transfer factor may include any type of transfer factor, as well as a combination of two or more types of transfer factor.

For example, avian transfer factor, bovine transfer factor, or any other type of transfer factor may be included in the transfer factor component. The transfer factor of the transfer component factor may be derived from any suitable, acceptable source. For example, avian transfer factor may be obtained from eggs, such as by a process disclosed in U.S. Pat. No. 6,468,534 to Hennen et al. (hereinafter "Hennen"), the disclosure of which is hereby incorporated herein, in its entirety, by this reference. An example of the manner in which bovine transfer factor may be obtained is disclosed in U.S. Pat. No. 4,816,563 to Wilson et al. (hereinafter "Wilson"), the disclosure of which is hereby incorporated herein, in its entirety, by this reference. Compositions that include two or more types of transfer factor, as well as processes for combining and processing two or more types of transfer factor, are disclosed in U.S. Pat. No. 6,866,868 to Lisonbee et al. (hereinafter "Lisonbee"), the disclosure of which is hereby incorporated herein, it its entirety, by this reference.

Transfer factor is known or believed to improve the oxidative balance of a living being, as well as to enhance the effectiveness of antioxidants, as demonstrated by the disclosure of the international patent application filed pursuant to the Patent Cooperation Treaty and having International Publication Number WO 2004/041071 A2 (hereinafter "Dadali"), the disclosure of which is hereby incorporated herein, in its entirety, by this reference.

As an alternative to transfer factor, the immune modulator of various embodiments of a nutraceutical food product of the present invention may comprise a nanofraction immune modulator of the type disclosed by U.S. patent application Ser. No. 11/855,944.

Other embodiments of nutraceutical food products of the present invention may include a plurality of different immune modulators, such as combinations of transfer factor and nanofraction immune modulators. Various examples of compositions that include transfer factor and nanofraction immune modulators are also disclosed by U.S. patent application Ser. No. 11/855,944.

A nutraceutical food product of the present invention may also include one or more preservatives. Suitable preservatives, such as those accepted for use in foods and beverages, may be used. Any preservatives that are included in a nutraceutical food product of the present invention may be able to withstand pasteurization processes. Examples of preservatives that may be included in an edible preparation of the present invention include, but are not limited to, sodium benzoate and preservatives from the paraben family of chemicals.

A particular embodiment of gel-based nutraceutical food product that incorporates teachings of the present invention is described in the following example:

Example 1

TABLE 1

| Ingredient | % of Total (w/w) | Density (g/ml) | % of Total Juices (v/v) |
|---|---|---|---|
| Water | 75.490 | 1.000 | |
| RioVida Juice Blend | 15.965 | | |
| Apple Juice | | 1.346 | 19 |
| Purple Grape Juice | | 1.330 | 19 |
| Blueberry Juice | | 1.315 | 18 |
| Pomegranate Juice | | | |
| Elderberry Juice | | 1.315 | 15 |
| Açai Powder | 0.325 | | 14 |
| Transfer Factor Tri-Factor Blend | 1.880 | | |
| Glycerine (Vegetable) | 4.210 | 1.249 | |
| Grape color concentrate (e.g., MEGANATURAL ™ purple from Canandaigua Concentrates & Colors, a Division of Canandaigua Wine Company of Madera, California) | 0.510 | 1.306 | |
| Vitamin C | 0.190 | | |
| Flavorings | 0.428 | | |
| Berry flavor (BE-01407) | | 1.000 | |
| Berry flavor (BE-01271) | | 1.000 | |
| Natural Vanilla (VA-01239) | | 1.000 | |
| Monolaurin (glycerol monolaurate) | 0.002 | | |
| Gums (Xanthan and Guar Gum, at a ratio of 1:1 w/w) | 1.000 | | |

Transfer Factor Tri-Factor Blend includes transfer factor (including bovine transfer factor from cow colostrum and avian transfer factor from the yolk of a chicken's egg) and nanofraction immune modulators.

The flavorings listed in TABLE 1 are available from Flavors Inc.

Glycerol monolaurate is a surfactant. A surfactant may be useful for maintaining homogeneity (i.e., for keeping the components of the nutraceutical food product, including, but not limited to, any immune support component present in the nutraceutical food product, dispersed substantially homogeneously throughout the nutraceutical food product).

A daily dosage of about one fluid ounce (about 30 ml) or more (e.g., about two fluid ounces, or 60 ml, etc.) of a composition with ingredients in the proportions listed in TABLE 1 may be administered to or consumed by a subject. In addition to the numerous known and believed benefits of antioxidants, including the benefits of OPC and OPC-containing fruits such as açai, administration or consumption of a nutraceutical food product that incorporates teachings of the present invention provides the subject with the additional and sometimes synergistic beneficial effects of transfer factor, which are known in the art, as evidenced by the disclosures of Dadali, Hennen, Lisonbee, and Wilson, and of nanofraction immune modulators.

An edible preparation may be made by mixing components of a food base with transfer factor by processes that are known in the art. Suitable processes that may be used to manufacture edible preparations of a variety of different forms are well known and within the skill of those in the relevant art. Known techniques, such as those disclosed in "Principles and Practices of Small- and Medium-Scale Fruit Juice Processing," Food and Agricultural Organization of the United Nations (FAO) Services Bulletin 146 (Rome, 2001), the entire disclosure of which is hereby incorporated herein by this reference, may be used in one or more parts of a process for manufacturing various embodiments of nutraceutical food products of the present invention.

Processes that are used to manufacture nutraceutical food products according to the present invention may be effected at a low temperature (e.g., between about 0° C. and about 10° C., at about 4° C., etc.), such as in a refrigerated environment, then transported and stored at such temperatures to reduce the likelihood of microbial growth or proliferation therein.

Alternatively, a nutraceutical food product that is in a form that is not completely dry may be pasteurized or sterilized. Pasteurization processes, which decrease the number of microorganisms present, but do not entirely eliminate the microorganisms, improve the stability of products that are to be stored at reduced temperatures (e.g., frozen or refrigerated, or "chilled"). When a nutraceutical food product is sterilized, all or substantially all microorganisms therein are killed or inactivated, facilitating prolonged storage of the nutraceutical food product at room temperature or even higher temperatures.

As an example, a nutraceutical food product that includes transfer factor and/or nanofraction immune modulators may be sterilized by known superheated steam injection processes. The temperatures and durations of such processes depend, of course, upon the form and ingredients of the composition to be sterilized. When making a liquid preparation, the resulting nutraceutical food product may be "flash" heated to a particular temperature (e.g., 250° F.) for a corresponding duration (e.g., two seconds). Alternatively, a sterilization or pasteurization process of different duration and temperature may be used, so long as the duration and temperature of the process are in substantial accord with a practice that has been accepted in the art, such as use of the following equation:

$$t_p = 5 \cdot 10^{14} \cdot e^{-0.4353 \cdot T_{mo}},$$

where $t_p$ is the minimum duration of the process, and $T_{mo}$ is the temperature at which the process is effected.

Of course, processes that reduce microbial load on a nutraceutical food product of the present invention need not comprise heat-treatment techniques. Sterilization or other microbial load-reducing techniques that employ other means (e.g., filtration, antimicrobial ingredients, etc.) may also be used in manufacturing a nutraceutical food product. Examples of suitable processes are disclosed in Hughes, D. E., and Nyborg, W., "Minimally Processed Fruits and Vegetables: Reducing Microbial Load by Nonthermal Physical Treatments," Food Technology 52(6): 66-71 (1997), the disclosure of which is hereby incorporated herein, in its entirety, by this reference.

It is desirable that, following pasteurization or sterilization, the transfer factor and/or nanofraction immune modulators retain some if not substantially all or all of their activity. A variety of pasteurization or sterilization processes may be employed, including pasteurization or sterilization processes that may be used to reduce microbial counts or completely eliminate microorganisms from foods. As many sterilization processes are known to significantly reduce the activity of certain proteins, including antibodies, a study was performed to determine whether transfer factor retains at least some of its activity following pasteurization.

In the study, mouse footpad assay techniques, similar to those disclosed in J. Natl. Cancer Inst. 55(5):1089-95 (November 1975), were used to determine the affects of heat pasteurization or sterilization processes (specifically, superheated steam injection processes) on liquid nutraceutical food products including transfer factor. Two sterilized samples were compared with an unsterilized sample, as well as with a negative control and a positive control.

Separate populations of six mice were tested for each of the five samples and controls. The tests were conducted in two phases, a first that immediately followed heat sterilization of the samples, and a second that was conducted after storing the two heat sterilized samples at a temperature of about 40° C. for about three months, which is well-accepted in the art to be the equivalent of about one year of storage at room temperature. Thirty different mice were used in each phase of the study. The following procedures were followed in each phase of the study.

In the positive control (i.e., the "fifth group"), fourteen days prior to testing, the footpads of the right rear feet of six BALB/c mice having ages of about nine weeks to about ten weeks were anesthetized with isoflurane. Then 0.02 ml of an about 50/50 (wt/wt) mixture of Freund's adjuvant and bovine rhinotracheitis virus diarrhea vaccine was administered intramuscularly to each mouse by way of two injections at the base of each side of the mouse's tail. This early injection of antigen allows the mice of the positive control group to elicit their own primary immune response and secondary, or delayed-type hypersensitivity response to the antigen. The mice of the other five groups were not preexposed to the antigen in this manner.

About twenty-four hours before evaluating the hind footpads of the mice, the six BALB/c mice of each group, which were of similar age to the mice of the positive control group, were anesthetized with isoflurane. About 0.5 ml of a sample solution or control solution was then administered by subcutaneous injection at the back of the neck of each mouse.

In the first group (see EXAMPLE 2 below), which was the negative control group, the back of the neck of each mouse was injected with about 0.5 ml of sterile saline solution.

In the second group (see EXAMPLE 3 below), the sample solution included 16% solids (w/v) of a reconstituted (in distilled, deionized water) lyophilized colostrum fraction that included transfer factor. The solution was set at a pH of 4.0, which was intended to estimate the pH of a fruit juice preparation (the actual pH of which is about 3.6 or about 3.7). Following reconstitution and pH adjustment, the solution was sterilized by heating the same to a temperature of 250° F. for about two seconds.

In the third group (see EXAMPLE 4 below), the sample solution included 16% solids (w/v) of a reconstituted (in distilled, deionized water) lyophilized colostrum fraction that included transfer factor. The pH of the resulting solution was not adjusted and, thus, was neutral (i.e., 7.0) or slightly basic (i.e., greater than 7.0)). Following reconstitution, the solution was sterilized by heating the same to a temperature of 250° F. for about two seconds.

In the fourth group (see EXAMPLE 5 below), the sample solution was a concentrate of a colostrum fraction that included transfer factor, which had been diluted to about 16% solids (w/v) in distilled, deionized water. This solution was not heat sterilized or pH adjusted.

The mice of the fifth group (see EXAMPLE 6 below), which was the positive control groups, respectively, received sterile saline solution.

At the start of the mouse footpad assay, the right hind footpad and the left hind footpad of each mouse were measured, such as with a Starrett gauge. The right hind footpad of each of the thirty mice during each phase of the study was then subcutaneously injected with an antigen-containing solution. The footpad on the left hind foot of each of the thirty mice in each phase, which was used as a control, was injected with about the same volume of a control solution, such as a sterile saline diluent, as the volume of antigen-containing solution that was injected into right hind footpad.

After a sufficient amount of time (e.g., about twenty-four hours) for the secondary immune response components of the immune system of each mouse to respond, each mouse was again anesthetized and the distances across right and left hind footpads were again measured. A significant amount of swelling, determined by an increase in the distance across a right hind footpad of a mouse from the initial measurement to the second measurement, is indicative of the occurrence of a delayed-type hypersensitivity reaction in that footpad.

The results of the mouse foot pad assays, and some accompanying analysis, are set forth in EXAMPLES 2 through 5 and 7:

Example 2

In the first phase of the study, the footpads on the right hind feet of the six mice of the negative control, or first group, exhibited, on average, about 6.35 micrometers more swelling about twenty-four hours after they were injected with the antigen solution than the swelling measured in the footpads of the left hind feet of these mice, which were merely inoculated with sterile saline.

The results for the negative control group during the second phase of the study are set forth in the following table:

TABLE 2

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1930.40 | 1955.80 | 25.40 |
|   | Right (test)   | 1905.00 | 1930.40 | 25.40 |
| 2 | Left (control) | 1981.20 | 2006.60 | 25.40 |
|   | Right (test)   | 2006.60 | 2057.40 | 50.80 |
| 3 | Left (control) | 2057.40 | 2057.40 | 0.00 |
|   | Right (test)   | 2032.00 | 2057.40 | 25.40 |
| 4 | Left (control) | 2006.60 | 2032.00 | 25.40 |
|   | Right (test)   | 2032.00 | 2057.40 | 25.40 |
| 5 | Left (control) | 1955.80 | 2006.60 | 50.80 |
|   | Right (test)   | 1930.40 | 1955.80 | 25.40 |
| 6 | Left (control) | 1905.00 | 1930.40 | 25.40 |
|   | Right (test)   | 1876.60 | 1955.80 | 76.20 |

Similar to the results from the first phase, the footpads of the right hind feet of the mice of the negative control group exhibited, on average, only 12.70 micrometers more swelling about twenty-four hours after antigen injection than the footpads of the left hind feet of the same mice exhibited twenty-four hours after sterile saline injection. As twenty-four hours is not a sufficient period of time for a mouse to mount a primary (i.e., antibody-mediated) immune response to the antigen, these insignificant differences in swelling show that the mice did not exhibit a significant secondary immune response to the antigen.

Example 3

In the first phase of the study, about twenty-four hours after they were injected with the antigen solution, the footpads on the right hind feet of the six mice of the second group of mice (which mice had previously been inoculated with a solution including 16% solids (w/v) colostrum at pH=4.0) swelled, on average, by 50.80 micrometers more than the swelling that was measured in the footpads of the left hind feet of these mice. These results indicate that there was a greater secondary, or delayed-type hypersensitivity, immune response in the footpads into which antigen was injected than in the footpads into which no antigen was injected, which were likely swollen merely because they were pierced by a needle.

In the second phase of the study, similar results were obtained, as set forth in the following table:

TABLE 3

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1955.80 | 2006.60 | 50.80 |
|   | Right (test)   | 1981.20 | 2057.40 | 76.20 |
| 2 | Left (control) | 1930.40 | 2006.60 | 76.20 |
|   | Right (test)   | 1955.80 | 2108.20 | 152.40 |
| 3 | Left (control) | 1955.80 | 2006.60 | 50.80 |
|   | Right (test)   | 1981.20 | 2082.80 | 101.60 |
| 4 | Left (control) | 2032.00 | 2057.40 | 25.40 |
|   | Right (test)   | 2057.40 | 2108.20 | 50.80 |
| 5 | Left (control) | 1930.40 | 2006.60 | 76.20 |
|   | Right (test)   | 1955.80 | 2032.00 | 76.20 |
| 6 | Left (control) | 2057.40 | 2108.20 | 50.80 |
|   | Right (test)   | 2032.00 | 2159.00 | 127.00 |

More specifically, the footpads of the right hind feet of the six mice of the second group swelled so that they measured, on average, 42.33 micrometers more than the swelling that was measured in the footpads of the left hind feet of these mice before and after inoculation of their foot pads with the antigen solution. The similar results between the first and second phases of the study indicate that, once a liquid solution that includes transfer factor has been heat sterilized, there is little or no change in the activity of the transfer factor after prolonged storage of the solution.

Example 4

The results for the third group of mice (which mice had previously been inoculated with a solution including 16% solids (w/v) colostrum at normal pH) were similar to the results for the second group in the first and second phases of the study.

In the first phase of the study, about twenty-four hours after the footpad injections, the antigen solution-inoculated footpads on the right hind feet of the six mice of the third group of mice swelled, on average, by 35.98 micrometers more than the swelling that was measured in the sterile saline-inoculated footpads of the left hind feet of these mice. These results indicate that there was a greater secondary, or delayed-type hypersensitivity, immune response in the footpads into which antigen was injected than in the footpads into which no antigen was injected, which were likely swollen merely because they were pierced by a needle.

In the second phase of the study, similar results were obtained, as set forth in the following table:

TABLE 4

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 2006.60 | 2032.00 | 25.40 |
|   | Right (test)   | 2032.00 | 2082.80 | 50.80 |
| 2 | Left (control) | 2057.40 | 2057.40 | 0.00 |
|   | Right (test)   | 2006.60 | 2108.20 | 101.60 |
| 3 | Left (control) | 1981.20 | 2006.60 | 25.40 |
|   | Right (test)   | 2057.40 | 2082.80 | 25.40 |
| 4 | Left (control) | 2006.60 | 2057.40 | 50.80 |
|   | Right (test)   | 2032.00 | 2082.80 | 50.80 |
| 5 | Left (control) | 2057.40 | 2082.80 | 25.40 |
|   | Right (test)   | 2082.80 | 2159.00 | 76.20 |
| 6 | Left (control) | 2082.80 | 2108.20 | 25.40 |
|   | Right (test)   | 2108.20 | 2159.00 | 50.80 |

These results show that the footpads of the right hind feet of the six mice of the third group swelled so that they measured, on average, 33.87 micrometers more than the swelling that was measured in the footpads of the left hind feet of these mice before and after inoculation of the foot pads with the antigen solution. The similar results between the first and second phases of the study indicate that, following prolonged storage, there was little or no change in the activity of the transfer factor in a heat-sterilized solution.

Example 5

These results were confirmed by the results that were obtained from the fourth group of mice. In particular, during the first phase of the study, the footpads of the right hind feet of mice in the fourth group (which included mice that had been inoculated with a diluted liquid colostrum fraction that was not heat sterilized) exhibited, on average, about 35.98 micrometers more swelling than the foot pads of left hind feet of these mice about twenty-four hours after these footpads had been inoculated with antigen solution and sterile saline, respectively.

Similar results were obtained during the second phase of the study, in which the average difference was 42.33 micrometers, as evidenced by the following data:

TABLE 5

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1955.80 | 2032.00 | 76.20 |
|   | Right (test) | 1981.20 | 2082.80 | 101.60 |
| 2 | Left (control) | 2006.60 | 2057.40 | 50.80 |
|   | Right (test) | 2032.00 | 2108.20 | 76.20 |
| 3 | Left (control) | 1955.80 | 2006.60 | 50.80 |
|   | Right (test) | 1930.40 | 2057.40 | 127.00 |
| 4 | Left (control) | 1955.80 | 2082.80 | 127.00 |
|   | Right (test) | 1905.00 | 2032.00 | 127.00 |
| 5 | Left (control) | 2032.00 | 2082.80 | 50.80 |
|   | Right (test) | 2057.40 | 2184.40 | 127.00 |
| 6 | Left (control) | 1955.80 | 1955.80 | 0.00 |
|   | Right (test) | 2006.60 | 2057.40 | 50.80 |

As these results are comparable to (i.e., not significantly greater than) those obtained with heat-sterilized solutions (see the results from EXAMPLES 3 and 4), it is apparent that heat sterilization of a solution that includes transfer factor does not significantly diminish or reduce the activity of the transfer factor.

Example 6

This conclusion was verified by data from another mouse footpad assay, in which six BALB/c mice were inoculated, behind the neck, with 0.5 ml of a solution including 16% solids (w/v) of a spray-dried colostrum fraction that had been reconstituted in distilled, deionized water. About twenty-four hours later, the mice were anesthetized with isoflurane, then footpads on their hind feet measured and inoculated in the manner described above (i.e., left footpad with sterile saline, right footpad with the antigen solution). After about another twenty-four hours, the footpads were again measured. The right footpads of these mice swelled, on average, about 42.33 micrometers more than the footpads on the left hind feet of these mice. This value is comparable to (i.e., not significantly different from) the differences noted above with respect to the second, third, and fourth groups of mice in both the first and second phases of the study detailed in EXAMPLES 2 through 5 and 7, further supporting the conclusion that heat sterilization of a solution that includes transfer factor, such as the solutions that were tested on the second and third groups of mice (EXAMPLES 3 and 4) does not have a significant adverse affect on the activity of the transfer factor.

Example 7

The fact that the transfer factor with which the mice were inoculated was responsible for the increased secondary immune response is supported by the results from the fifth group, or positive control group, of mice during the second phase of the study, as set forth in the following table:

TABLE 6

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1981.20 | 2006.60 | 25.40 |
|   | Right (test) | 2006.60 | 2082.80 | 76.20 |
| 2 | Left (control) | 1828.80 | 1854.20 | 25.40 |
|   | Right (test) | 1879.60 | 2082.80 | 203.20 |
| 3 | Left (control) | 1905.00 | 1930.40 | 25.40 |
|   | Right (test) | 1981.20 | 2082.80 | 101.60 |
| 4 | Left (control) | 2006.60 | 2057.40 | 50.80 |
|   | Right (test) | 2032.00 | 2184.40 | 152.40 |
| 5 | Left (control) | 2032.00 | 2057.40 | 25.40 |
|   | Right (test) | 2057.40 | 2184.40 | 127.00 |
| 6 | Left (control) | 2108.20 | 2108.20 | 0.00 |
|   | Right (test) | 2082.80 | 2184.40 | 101.60 |

These results, which show on average, 101.60 micrometers more swelling in the footpads that were inoculated with antigen solution over those that were inoculated with sterile saline, are similar to the 124.88 micrometer difference seen in the mice of the positive control group during the first phase of the mouse footpad study. The greater swelling in the antigen solution-inoculated footpads of the mice of the positive control group is indicative of a greater secondary immune response than that induced artificially by administration of transfer factor, as the mice of the positive control group had a sufficient period of time (i.e., two weeks) to generate their own transfer factor and, thus, to mount their own secondary immune response to the antigen.

Once a nutraceutical food product of the present invention has been manufactured, it may be introduced into a clean or sterile container for subsequent transport and storage.

Example 8

In another study, mouse footpad assays were conducted to determine the effectiveness of transfer factor in heat-treated samples of a liquid solution that included transfer factor that had been stored for one year. In total, four samples were prepared, two each having a pH of about 4 and two each having a pH of about 7. All of the samples had been flash sterilized at a temperature of about 250° F. for about two seconds to about four seconds. The samples were subsequently stored for one year, with one each of the pH=4 and pH=7 samples having been stored at room temperature (which varied from about 65° F. to about 74° F.) and one each of the pH=4 and pH=7 samples having been refrigerated (at temperatures of about 40° F.). After one year, the samples were lyophilized. Prior to testing, the lyophilized samples were reconstituted to desired concentrations, then administered in the manner described above.

In a first sample, which included liquid having a pH of about 4 that was stored at room temperature, footpad swelling was, on average, 50.80 micrometers greater in footpads that had been injected with antigen versus footpads that had merely been injected with saline. These results were repeated in second (liquid of a pH of about 7 that was stored at room temperature), third (liquid of a pH of about 4 that was refrigerated), and fourth (liquid of a pH of about 7 that was refrigerated) samples, in which hind footpads that had been injected with antigen were, on average, respectively swollen 59.27, 67.73, and 63.50 micrometers more than hind footpads that were merely injected with saline.

Additionally, positive and negative controls were prepared as discussed above. In the positive control, the average difference in swelling between antigen-injected footpads and saline-injected footpads was 114.30 micrometers. In the negative control, the average difference in swelling between antigen-injected footpads and saline-injected footpads was only 38.10 micrometers.

Taken together, these data indicate that the increased swelling was due to the presence of transfer factor in the mice in the areas (hind footpads) into which antigen was introduced. Additionally, these data indicate that the transfer factor lost little or none of its effectiveness after heat-treatment and prolonged storage. The activity of transfer factor in refrigerated samples appears to have been slightly higher than the activity of transfer factor in the room temperature samples.

Further, it appears from the foregoing that the pH at which the transfer factor is maintained (about 4 or about 7) has little or no effect on its long term viability.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A composition comprising:
   a gel, an oligomeric proanthocyanidin and a transfer factor, wherein the oligomeric proanthocyanidin is dispersed throughout the gel, the transfer factor is dispersed throughout the oligomeric proanthocyanidin and the oligomeric proanthocyanidin is from acai.

2. The composition of claim 1, wherein the gel comprises xanthan and guar gum.

3. The composition of claim 1, wherein the gel comprises xanthan, guar gum and pectin.

4. The composition of claim 3, wherein the pectin comprises fruit pectin.

5. The composition of claim 1, wherein the composition further comprises at least one of an additional oligomeric proanthocyanidin-containing fruit juice or an oligomeric proanthocyanidin-containing fruit extract.

6. The composition of claim 5, wherein the additional oligomeric proanthocyanidin-containing fruit juice or the oligomeric proanthocyanidin-containing fruit extract is derived from at least one of elderberry, grape or pomegranate.

7. The composition of claim 1, further comprising a surfactant.

8. The composition of claim 7, wherein the surfactant comprises glycerol monolaurate.

9. The composition of claim 1, further comprising a preservative.

10. The composition of claim 9, wherein the preservative is selected from the group consisting of sodium benzoate and paraben.

11. The composition of claim 1, wherein the transfer factor includes avian transfer factor and/or bovine transfer factor.

12. The composition of claim 11, wherein the transfer factor comprises avian transfer factor obtained from avian egg.

13. The composition of claim 1, wherein the composition is sterile.

14. The composition of claim 1, wherein the gel comprises a gelling agent.

15. The composition of claim 1, wherein the gel comprises gelatin.

16. A nutritional supplement comprising:
    a gel, an oligomeric proanthocyanidin and a transfer factor, wherein the oligomeric proanthocyanidin is dispersed throughout the gel, the transfer factor is dispersed throughout the oligomeric proanthocyanidin and the oligomeric proanthocyanidin is from acai.

17. A nutritional supplement comprising:
    a gel, an oligomeric proanthocyanidin and a transfer factor, wherein the oligomeric proanthocyanidin is dispersed throughout the gel, the transfer factor is dispersed throughout the oligomeric proanthocyanidin.

* * * * *